US010105519B2

(12) United States Patent
Chanduszko

(10) Patent No.: US 10,105,519 B2
(45) Date of Patent: Oct. 23, 2018

(54) VARIABLE DIAMETER MEDICAL BALLOON

(71) Applicant: C.R. BARD, INC., Tempe, AZ (US)

(72) Inventor: Andrzej J. Chanduszko, Chandler, AZ (US)

(73) Assignee: C.R. BARD, INC., Tempe, AZ (US)

( * ) Notice: Subject to any disclaimer, the term of this patent is extended or adjusted under 35 U.S.C. 154(b) by 306 days.

(21) Appl. No.: 14/887,919

(22) Filed: Oct. 20, 2015

(65) Prior Publication Data
US 2017/0106173 A1 Apr. 20, 2017

(51) Int. Cl.
*A61M 25/10* (2013.01)
*A61M 25/09* (2006.01)
*A61B 17/22* (2006.01)

(52) U.S. Cl.
CPC ............ *A61M 25/10* (2013.01); *A61M 25/09* (2013.01); *A61M 25/104* (2013.01); *A61M 25/1018* (2013.01); *A61B 17/22* (2013.01); *A61B 2017/22001* (2013.01); *A61B 2017/22062* (2013.01)

(58) Field of Classification Search
CPC ........ A61B 2017/22001; A61M 25/10; A61M 25/1002; A61M 25/104; A61M 2025/1004; A61M 2025/1059; A61M 2025/1068; A61M 2025/107; A61M 2025/1081; A61F 2/97
See application file for complete search history.

(56) References Cited

U.S. PATENT DOCUMENTS

| | | | | |
|---|---|---|---|---|
| 5,049,131 A * | 9/1991 | Deuss | ............... | A61M 25/1002 604/103.02 |
| 5,746,745 A * | 5/1998 | Abele | ..................... | A61F 2/958 604/103.08 |
| 6,010,480 A * | 1/2000 | Abele | ..................... | A61F 2/958 604/103.06 |
| 6,746,425 B1 * | 6/2004 | Beckham | .............. | A61L 29/126 604/103.09 |
| 7,285,109 B2 * | 10/2007 | Wu | ....................... | A61M 25/10 604/103.03 |
| 7,309,324 B2 * | 12/2007 | Hayes | .................. | A61M 25/104 604/96.01 |
| 7,354,419 B2 * | 4/2008 | Davies, Jr. | .......... | A61M 25/104 604/103.06 |

(Continued)

*Primary Examiner* — Ryan J Severson
(74) *Attorney, Agent, or Firm* — King & Schickli, PLLC

(57) ABSTRACT

An apparatus for performing a medical procedure includes a balloon comprising an inflatable body. A first releasable or frangible connection is provided to maintain the body at a first diameter up to a first inflation pressure, and to release, such as by disconnecting, and thus allow the body to assume a second diameter, such as at a second inflation pressure greater than the first inflation pressure or upon a manual release of the connection by a clinician. Multiple releasable or frangible connections may be provided, including between portions (folds) of the inflatable body of the balloon. This disclosure also pertains to a non-compliant or semi-compliant balloon having a first inflation diameter corresponding to a first range of inflation pressures and a second inflation diameter corresponding to a second inflation pressure greater than the first range of inflation pressures.

6 Claims, 7 Drawing Sheets

(56) References Cited

U.S. PATENT DOCUMENTS

| | | | | |
|---|---|---|---|---|
| 7,682,335 B2* | 3/2010 | Pepper | A61L 29/085 | 604/103.09 |
| 7,879,005 B2* | 2/2011 | Wu | A61M 25/10 | 604/103.03 |
| 8,114,049 B2 | 2/2012 | Freyman et al. | | |
| 8,216,294 B2* | 7/2012 | Johnson | A61F 2/856 | 606/108 |
| 8,287,940 B2* | 10/2012 | Von Holst | A61L 29/16 | 427/2.1 |
| 8,308,749 B2* | 11/2012 | Johnson | A61F 2/856 | 606/108 |
| 8,658,239 B2* | 2/2014 | Von Holst | A61L 29/16 | 427/2.1 |
| 8,702,745 B2* | 4/2014 | Degen | A61F 2/958 | 604/103.07 |
| 8,845,675 B2* | 9/2014 | Johnson | A61F 2/856 | 606/108 |
| 9,126,035 B2* | 9/2015 | Valoir | A61N 5/1014 | |
| 2004/0162575 A1* | 8/2004 | Wu | A61M 25/10 | 606/194 |
| 2005/0059957 A1* | 3/2005 | Campbell | A61M 25/0043 | 604/524 |
| 2006/0085022 A1* | 4/2006 | Hayes | A61M 25/104 | 606/192 |
| 2006/0085023 A1* | 4/2006 | Davies, Jr. | A61M 25/104 | 606/192 |
| 2006/0085024 A1* | 4/2006 | Pepper | A61L 29/085 | 606/192 |
| 2007/0156166 A1* | 7/2007 | Wu | A61M 25/10 | 606/192 |
| 2009/0054837 A1* | 2/2009 | Von Holst | A61L 29/16 | 604/103.08 |
| 2009/0227949 A1* | 9/2009 | Knapp | A61L 29/085 | 604/103.02 |
| 2010/0152711 A1* | 6/2010 | Utke | A61F 2/95 | 604/528 |
| 2011/0295201 A1* | 12/2011 | Degen | A61F 2/958 | 604/103.06 |
| 2013/0066268 A1* | 3/2013 | Von Holst | A61L 29/16 | 604/103.08 |
| 2013/0109906 A1* | 5/2013 | Valoir | A61N 5/1014 | 600/3 |
| 2015/0012032 A1* | 1/2015 | Cox | A61M 25/1002 | 606/192 |
| 2017/0007805 A1* | 1/2017 | Tsubooka | A61B 17/22 | |
| 2017/0106173 A1* | 4/2017 | Chanduszko | A61M 25/10 | |

* cited by examiner

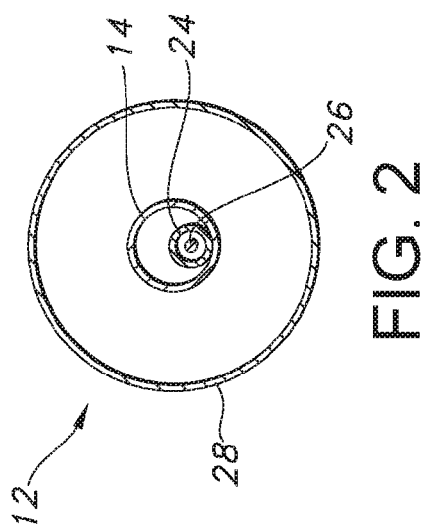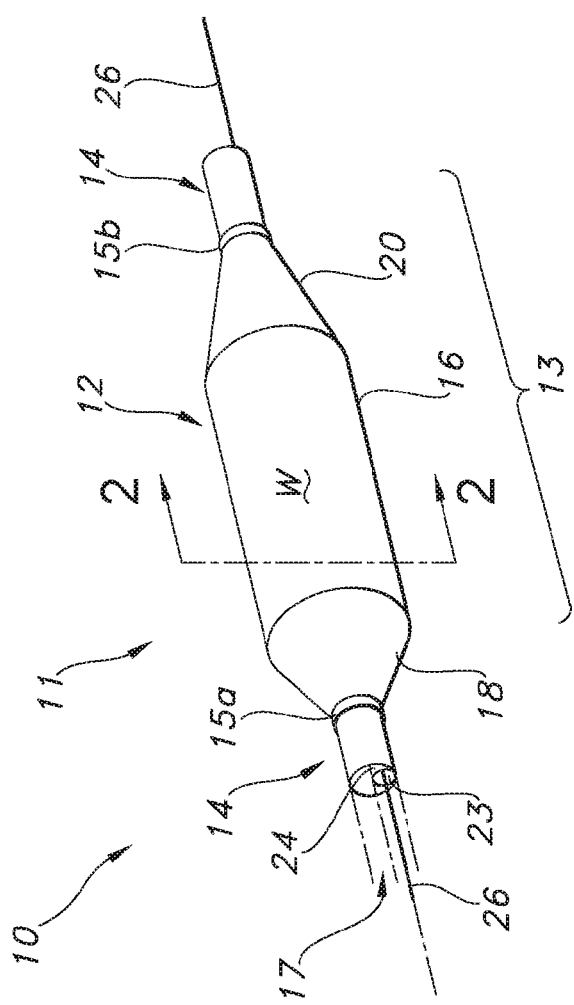

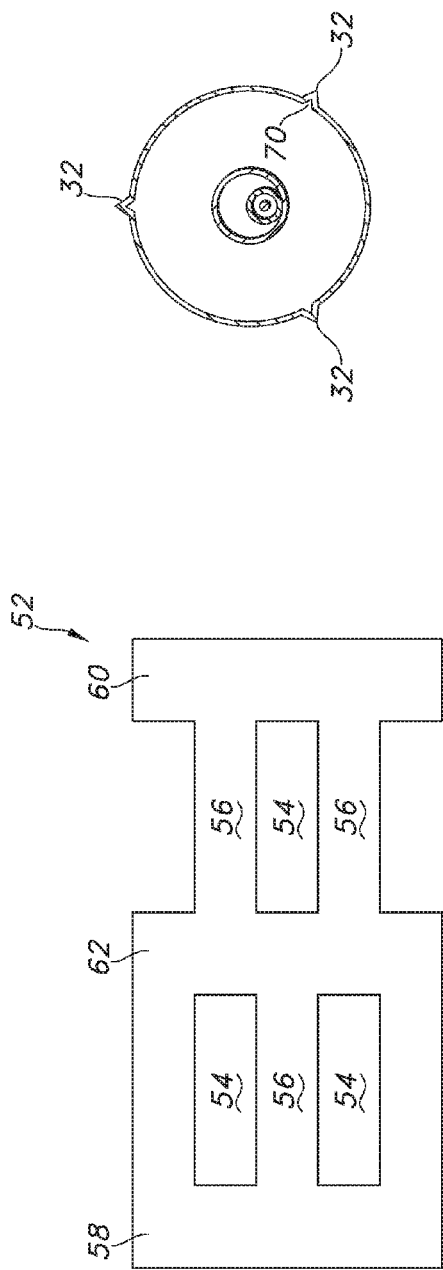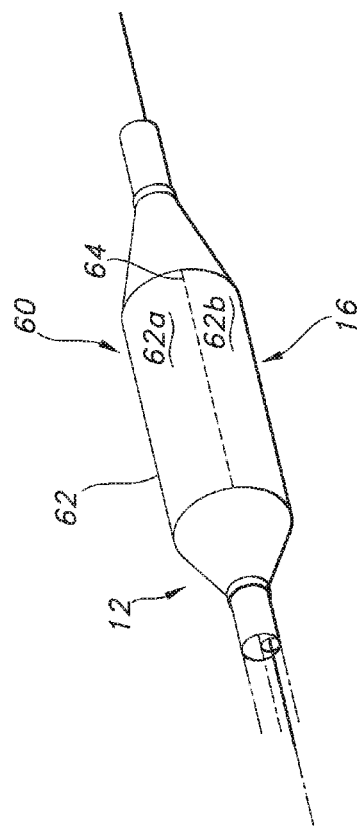

VARIABLE DIAMETER MEDICAL BALLOON

INCORPORATION BY REFERENCE

All publications and patent applications mentioned in this specification are herein incorporated by reference to the same extent as if each individual publication or patent application was specifically and individually indicated to be incorporated by reference.

BACKGROUND

Non-compliant medical balloons for performing angioplasty and other medical procedures are known. U.S. Pat. No. 6,746,425 to Beckham discloses a non-compliant medical balloon and methods for manufacturing the balloon. U.S. Patent Application Publication No. US 2006/0085022 to Hayes et al. discloses a non-compliant medical balloon having an integral woven fabric layer and methods for manufacturing the balloon. U.S. Patent Application Publication No. US 2006/0085023 to Davies, Jr. et al. discloses a medical balloon having strengthening rods and methods for manufacturing the balloon. U.S. Patent Application Publication No. US 2006/0085024 to Pepper et al. discloses a non-compliant medical balloon having an integral non-woven fabric layer and methods for manufacturing the balloon. U.S. Pat. No. 6,746,425 and Publication Nos. US 2006/0085022, US 2006/0085023 and US 2006/0085024.

During an intervention, the balloon is inserted into a vessel, typically on the end of a catheter, until the balloon reaches the area of interest. Adding pressure to the balloon causes the balloon to inflate. In one variation of use, the balloon creates an outwardly directed force when inflated, which can be used to treat a variety of conditions.

As can be appreciated, different applications (such as for treating different vessels or parts of the body) may require the use of balloons having different diameters when inflated. Currently, manufacturers make multiple balloons available for use with different inflation diameters, and the clinician must select the appropriate balloon under a given set of conditions. In some cases, the number of balloons available may be more than twenty, ranging widely in diameter when inflated (e.g., from 12-26 millimeters) for a variety of different vessel diameters. This clearly increases the demands on manufacturers to provide the full variety of balloons that might be required for use with different sizes of vessels (which can vary at the sub-millimeter level), and also adds complexity to the selection process by the clinician given the large number of options available. While fully compliant balloons may be used to provide a variety of diameters under different inflation pressures, this compliance makes such a balloon generally ineffective for providing the treatment in the desired manner, especially where a significant force is required.

Thus, it would be desirable to provide a single balloon that can be adjusted (including in situ) to treat a variety of vessel diameters in an effective and reliable manner.

SUMMARY OF THE DISCLOSURE

According to one aspect of the disclosure, an apparatus for performing a medical procedure comprises a balloon, which may be non-compliant or semi-compliant. The balloon may comprise an inflatable body and a first connection adapted to maintain the body substantially at a first diameter at a first inflation pressure, and to release or disconnect and thereby allow the body to expand to a second diameter. The first connection may be released upon a second inflation pressure greater than the first inflation pressure being applied to the inflatable body, or by manual intervention by a clinician.

The apparatus may include a second connection adapted to allow the body to assume the second diameter, such as by disconnecting second and third portions of the balloon (or possibly associated with the first and second portions as well). The second releasable connection may alternatively be adapted to allow the body to assume a third diameter, such as for example at a third inflation pressure greater than the second inflation pressure or as a result of manual intervention by a clinician.

The releasable connection(s) may take a variety of forms. For instance, the releasable connection may comprise an adhesive, and thus may be considered a form of a frangible connection. The connection may also comprise a first connector connected to the first portion and a second connector connected to the second portion and adapted for releasably engaging the first connector. The connection may also be provided in the form of a retainer with interdigitated portions for maintaining the balloon a desired configuration, such as at a first diameter. A line, such as a cord, may also be provided for releasing the releasable connection from a remote location, which line may extend though a lumen in a catheter shaft associated with the balloon.

According to a further aspect of the disclosure, an apparatus for performing a medical procedure includes a balloon comprising an inflatable body having a first fold held in place by a first connection adapted to release the fold upon the body being inflated. The first releasable connection is adapted to release the first fold upon the body being inflated to a predetermined inflation pressure. Thus, the body may be inflated to provide a first diameter prior to the release of the fold and a second diameter upon release of the fold.

The balloon may comprise a plurality of folds, each held in place by a releasable connection. Each releasable connection may be adapted to release the corresponding fold upon the body being inflated to a different inflation pressure. Alternatively, each releasable connection may be adapted to release the corresponding fold upon the body being inflated to a predetermined inflation pressure.

The first releasable connection may be adapted to hold the first fold in place while the balloon is inflated to a nominal or first diameter for treatment. The first fold may include a recessed portion between adjacent lobes, each of the lobes including a portion of the releasable connection.

According to a further aspect of the disclosure, an apparatus for performing a medical procedure is provided. The apparatus comprises a non-compliant or semi-compliant balloon having a first, substantially constant diameter corresponding to a first range of inflation pressures and a second diameter, which may be substantially constant, corresponding to a second inflation pressure greater than the first range of inflation pressures.

The balloon may further include a third diameter, which may also be substantially constant, corresponding to a third inflation pressure greater than the second inflation pressure. The balloon may comprise a first releasable connection adapted for retaining the balloon at the first diameter until the second inflation pressure is reached.

According to a further aspect of the disclosure, an apparatus for performing a medical procedure comprises a balloon comprising an inflatable body having a fold held in place by an adhesive. The disclosure is also considered to pertain to methods of treatment using any apparatus disclosed herein.

BRIEF DESCRIPTION OF THE DRAWING FIGURES

Reference is made below to the following drawing figures, which are not to scale and provided for purposes of illustration only:

FIG. 1 is a cutaway perspective view showing one embodiment of a balloon to which this disclosure may be applicable;

FIG. 2 is a cross-sectional view of the balloon of FIG. 1 along line 2-2;

FIGS. 12-16 illustrate further embodiments of various types of frangible or releasable connections for forming an adjustable diameter medical balloon.

DETAILED DESCRIPTION

The invention disclosed pertains to an inflatable balloon for performing a medical procedure. The novel features of the invention are set forth with particularity in the claims that follow. A better understanding of the features and advantages of the invention will be obtained by reference to the following detailed description that sets forth illustrative embodiments, in which the principles of the invention are utilized, and the accompanying drawings.

Figure 3:
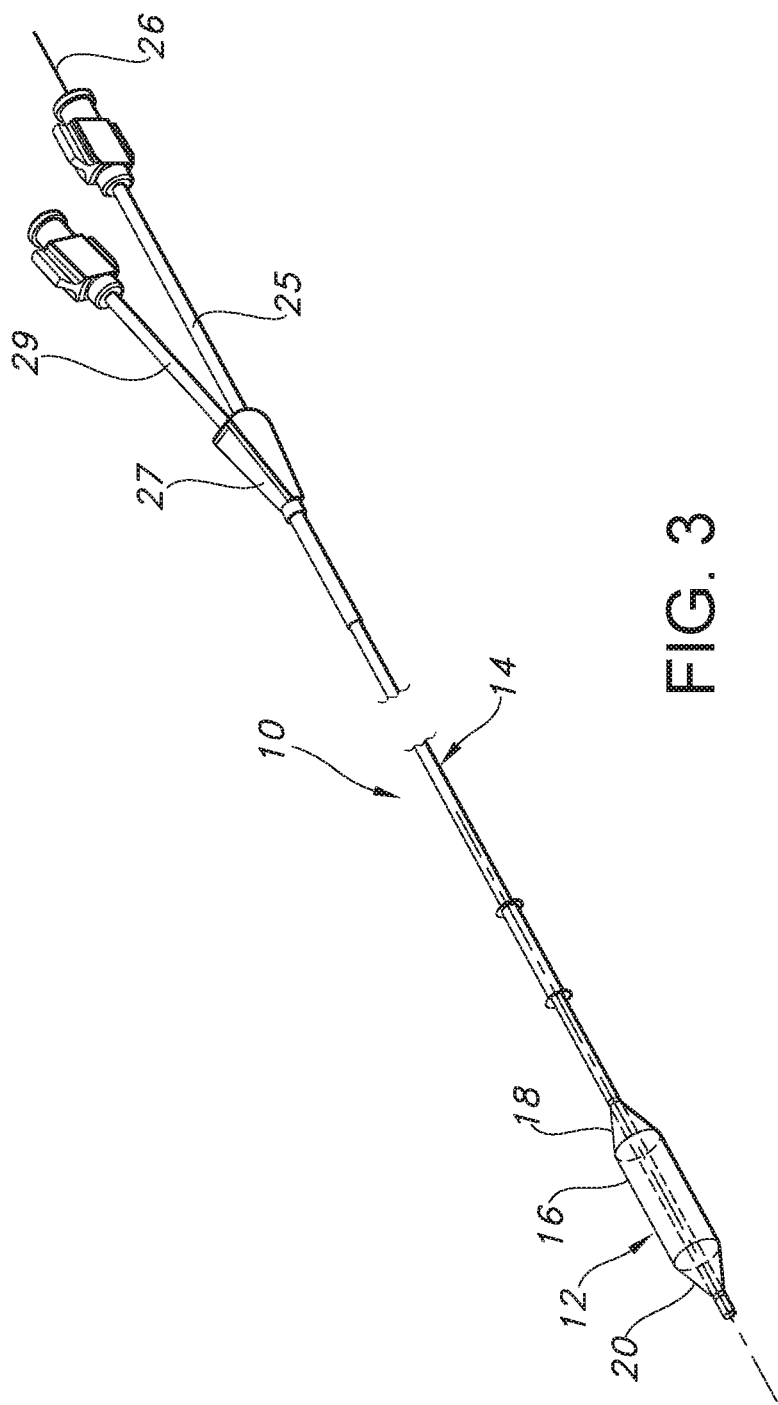
FIG. 3 is a perspective view of a catheter including the balloon of FIG. 1.

Provided is a catheter 10 having a distal portion 11 with a balloon 12 mounted on a catheter tube 14. Referring to FIGS. 1, 2, and 3, the balloon 12 has a body 13 including an intermediate section 16, or "barrel" having the working surface W, and end sections 18, 20. In one embodiment, the end sections 18, 20 reduce or taper in diameter to join the intermediate section 16 to the catheter tube 14 (and thus sections 18, 20 are generally termed cones or cone sections, and the barrel provides the working surface W). The balloon 12 is sealed to catheter tube 14 at balloon ends (proximal 15a and distal 15b) on the end sections 18, 20 to allow the inflation of the balloon 12 via one or more inflation lumens 17 extending within catheter tube 14 and communicating with the interior of the balloon 12.

Figure 4:
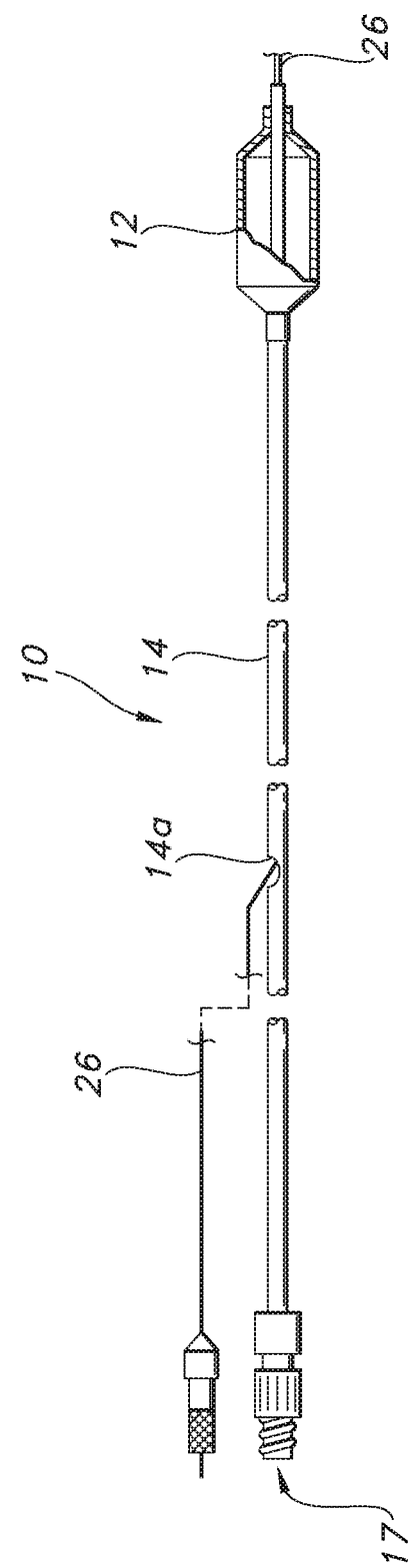
FIG. 4 is an alternate embodiment of a catheter including the balloon of FIG. 1.

The catheter tube 14 also includes an elongated, tubular shaft 24, which may form a lumen 23 that directs the guidewire 26 through the catheter 10. As illustrated in FIG. 3, this guidewire 26 may be inserted through a first port 25 of a connector, such as a hub 27, into the lumen 23 to achieve an "over the wire" (OTW) arrangement, but could also be provided in a "rapid exchange" configuration in which the guidewire 26 enters the lumen through a lateral opening 14a closer to the distal end (see FIG. 4). A second port 29 may also be associated with catheter 10, such as by way of connector (hub 27), for introducing a fluid (e.g., saline, a contrast agent, or both) into the interior of the balloon 12 via the inflation lumen 17.

Balloon 12 may include a single or multi-layered balloon wall 28. The balloon 12 may be a non-compliant balloon having a balloon wall 28 that maintains its size and shape in one or more directions when the balloon is inflated to a particular pressure or range of pressures (but below a rated burst pressure). However, the balloon 12 could be semi-compliant instead, as described in U.S. Pat. No. 8,900,215. Prior to use, the balloon wall 28 is typically folded to assume an uninflated diameter that is only slightly greater than the diameter of the catheter tube 14, which thus facilitates insertion into the vasculature.

According to one aspect of the disclosure, the balloon 12, despite being non-complaint or semi-compliant, may be adapted for being inflated from a fully folded or collapsed condition to different diameters for different purposes or uses. In one embodiment, and with reference to FIGS. 5 and 6, this may be achieved through the use of one or more releasable or frangible connections 30 adapted to retain the body 13 of the balloon 12 in a first configuration (such as corresponding to a first diameter) up to a first inflation pressure, and to release and thereby allow the body to assume a second configuration (such as corresponding to a second diameter). The release may occur upon the balloon 12 being inflated to a second inflation pressure greater than the first inflation pressure, or by way of a manual release, as outlined further in the following description. For purposes of this disclosure, "frangible" means readily or easily broken, and is not meant to limit the type of connection in any way.

Figure 5A:
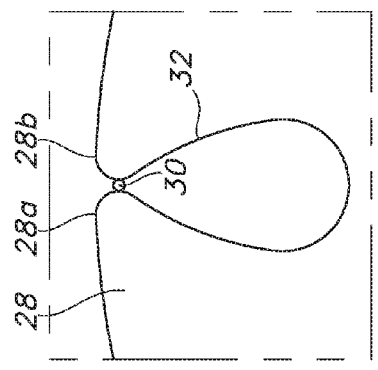
FIG. 5a is a close-up cutaway view of the balloon of FIG. 5.
Figure 5:
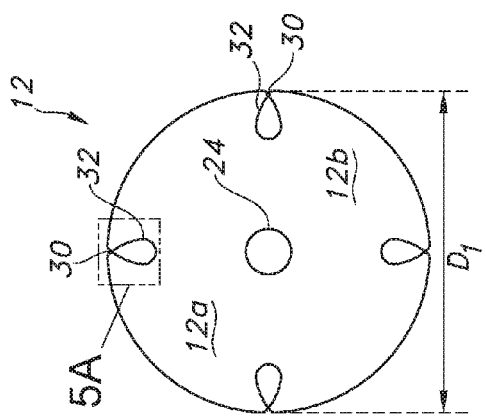
FIG. 5 is a schematic end view of a balloon according to one aspect of the disclosure, inflated to a first inflation pressure.
Figure 6:
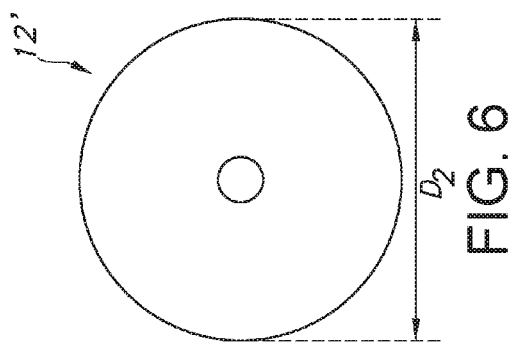
FIG. 6 is a schematic end view of the balloon of FIG. 5 in a fully inflated condition.

The connections 30 are shown as being formed between first and second portions 28a, 28b of the balloon wall 28, which may thus be arranged to create one or more folds 32. The folds 32 thus provide the balloon 12 with a corresponding number of lobes 12a, 12b when inflated to the first inflation pressure. The folds 32 may extend along all or a portion of the barrel section 16 of the balloon 12, and may form a recessed portion of the balloon, as perhaps best shown in FIG. 5a. In the embodiment of FIG. 5, four connections 30 are provided, thus giving the balloon 12 on inflation a quatrefoil shape in cross-section when the folds 32 comprise recessed portions, but more or fewer may be provided. It can be appreciated that the length of material of the balloon wall 28 forming the fold 32 corresponds directly to the increase in diameter achieved once the corresponding frangible connection 30 is released, and which length may be adjusted as desired during the manufacturing process to provide a greater or lesser increase in diameter.

Each connection 30 may comprise a bond adapted to disconnect or release, either from itself or from corresponding parts of the balloon 12, upon the inflation pressure reaching or exceeding a particular level. Thus, by way of example, the balloon 12 may be inflated from a collapsed or folded condition (which is normally the case during insertion to a treatment area in the vasculature) associated with no inflation pressure to a first inflation pressure (such as, for example, 6 atmospheres), and reach a first diameter D1 (such as for example 6 mm), as shown in FIG. 5. The balloon 12 may thus be used in this condition to treat a vessel having a corresponding diameter, which is typically less than the diameter on full inflation (e.g., 5 mm).

Applying a second inflation pressure (e.g., 8 atmospheres) greater than the first inflation pressure, or alternatively the pressure at which the connection(s) 30 would remain intact and maintain folds 32, would thus cause the balloon 12 to expand to a second diameter D2 (e.g., 9 mm, as indicated by reference numeral 12'). In this condition, as can be appreciated from FIG. 6, the folds 32 are disappeared and the balloon 12 along the barrel section 16 with the generally cylindrical cross-section has a substantially smooth and uninterrupted surface. This increased diameter may be used to treat a vessel having a different diameter (e.g., 8 mm), and may be created in situ during treatment.

Thus, it can be appreciated that, by using the releasable or frangible connections 30, a variable or adjustable diameter balloon 12 may be provided in a relatively simple and inexpensive manner, and which may eliminate the need for having different balloons corresponding to the treatment or vessel diameters at issue (5 mm and 8 mm in this example). It can also be understood that the balloon 12 may be characterized as a non-compliant or semi-compliant one designed to have a first, substantially constant diameter at a first range of inflation pressures (e.g., remaining at about 6 millimeters in diameter from 6 atmospheres up to 8 atmospheres), but then have a second diameter (e.g., 9 mm) at an inflation pressure greater than the first range (above 8 atmospheres). The difference in diameters may be considerable (i.e., 6 millimeters versus 9 millimeters, or about 33% different, but possibly less or perhaps even greater). Likewise, the balloon 12 may be considered as one that has a different cross-sectional shape at different inflation pressures (such as between the quatrefoil shape of FIG. 5 and the circular shape of FIG. 6).

Figure 7:
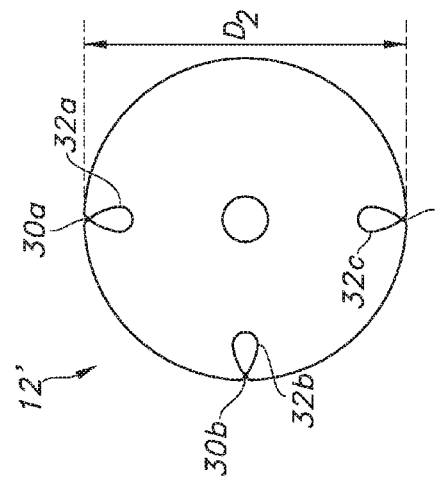
FIGS. 7-9 are schematic end views of balloons showing the reaction to a progressive increase of inflation pressures.
Figure 8:
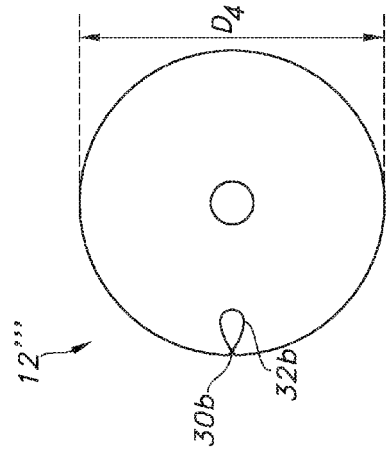
Figure 9:
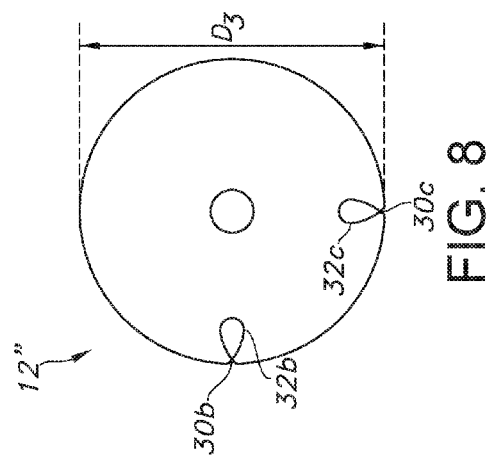

With reference to FIGS. 7-8, it can be appreciated that the balloon 12 may be adapted to expand to more than two diameters, such as by using different types of connections 30. Thus, for example, FIG. 7 illustrates a balloon 12 expanded to a second diameter D2 (not necessarily the same diameter as D2 in FIG. 6), and indicated by reference numeral 12'. In this condition, one fold may be substantially disappeared, as a result of the application of a first inflation pressure, but three folds 32a-32c remain intact as the result of connections 30a, 30b, 30c, which thus form bonds that require a force greater than that created by the first inflation pressure in order to be broken.

FIG. 8 illustrates the situation where the inflation pressure has been increased to at least a second level sufficient to break the bond created by connection 30a, which thus allows for fold 32a to disappear. The balloon 12 is thus expanded to a third diameter D3 greater than diameter D2, as indicated by reference number 12''. Connections 30b, 30c remain intact, as do associated folds 32b, 32c, for so long as the pressure does not rise to a level sufficient to break the corresponding bond(s) and thus further expand the diameter.

Additional pressurization to at least a third pressure level higher than the level necessary to remove connection 30a may cause further expansion to a fourth diameter D4, as indicated by reference number 12'''. This may involve breaking the bond created by frangible connection 30c, and thus expanding as a result of the unfurling of material of the balloon wall 28 associated with fold 32c. Fold 32b remains intact according to connection 30b, which is designed to withstand the third inflation pressure (and possibly a range exceeding it). As should be appreciated, frangible connection 30b could be designed to disconnect at the third pressure level, either instead of or in addition to the disconnection of connection 30c.

A frangible-type connection 30 may be provided by applying an adhesive between different portions of the balloon 12, such as along the outer surface of the balloon wall 28, to thus form the folds 32. The adhesive may be provided along some or all of the wall 28, including possibly within the material forming the fold 32, which may provide for the desirable differential pressure reactions in order to achieve the variable diameters. Multiple connections 30 may also be provided within a fold 32, which could allow for a single fold to provide multiple changes in balloon diameter.

Figure 10:
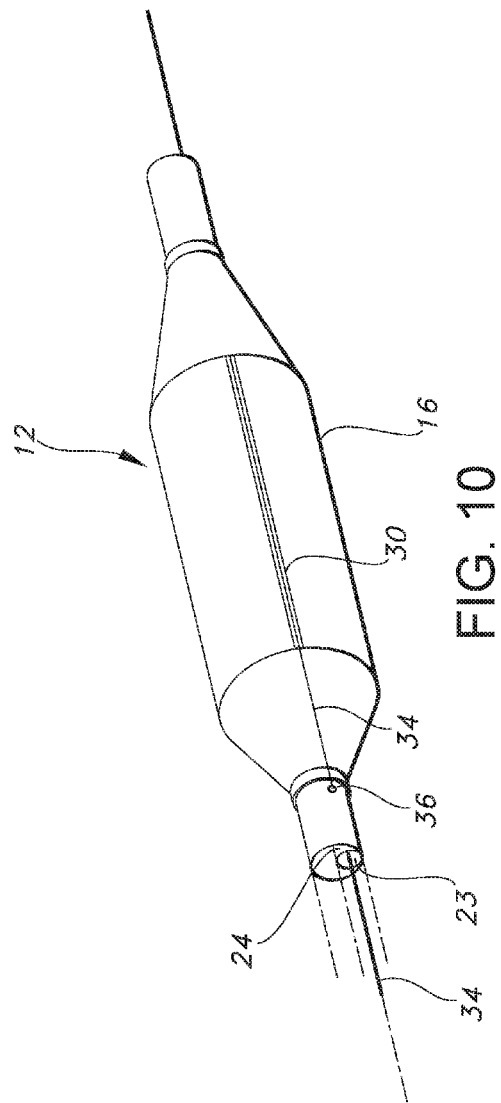
FIG. 10 illustrates a further embodiment of an adjustable diameter balloon.

FIG. 10 illustrates that the releasable or frangible connection 30 may be associated with a remotely controlled actuator, such as an elongated cord or line 34. The line 34 may extend along all or part of the connection 30 and pass along an external surface of the balloon 12 though an opening 36 and into a lumen 23 formed by a tube, such as tube 24. The line 34 may pass to an external point for manual manipulation by the clinician (similar to guidewire 26). In this manner, the release of the connection 30 and the resulting expansion of the balloon 12 may be actively controlled in situ. Furthermore, the expansion may occur without a corresponding change in the inflation pressure.

Figure 11:
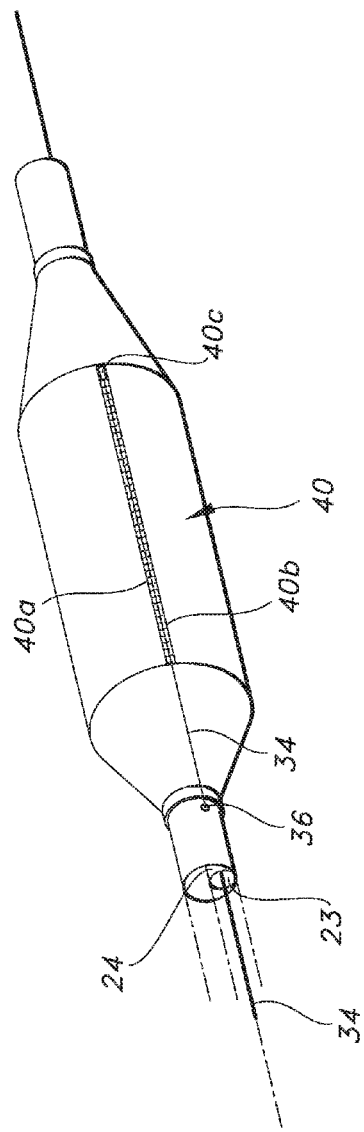
FIG. 11 illustrates still another embodiment of such a balloon.

In one embodiment, the line 34 may be embedded in an adhesive forming the frangible connection 30, and may thus form a pull or "rip" cord that facilitates to release the bond thus created. Alternatively, with reference to FIG. 11, a connector 40 may be provided between the balloon portions and forms the connection 30, which connector may be associated with the line 34. Thus, as illustrated, the connector 40 may comprise a zipper-like connection, with a first part 40a being attached to a first portion of the balloon 12, and a second part 40b being connected to a second portion of the balloon, and an actuator 40c for releasing the connector 40 connected to the distal end of the line 34. Still another alternative is to provide a non-adhesive connector (such as, for example, an embedded fiber) that forms a connection or bond among parts of the balloon 12 that is simply overcome by pressurization, without using line 34 and without intervention by the clinician (except of course for causing the increase in pressure).

Figure 12:
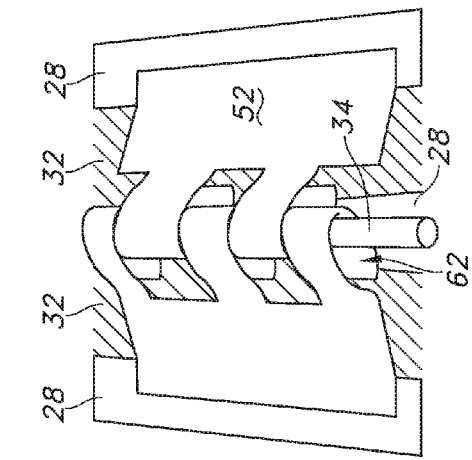
Figure 13:
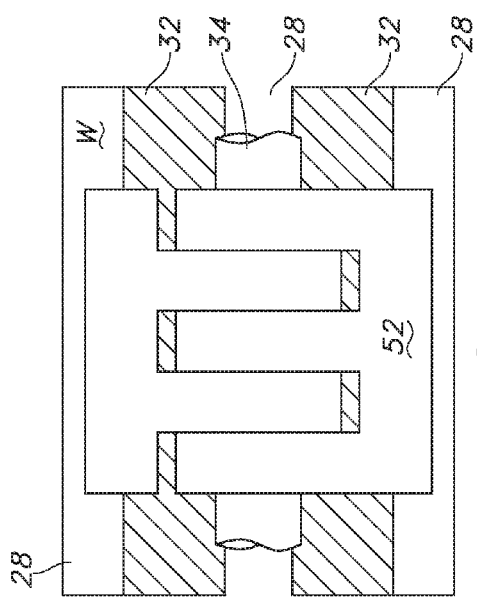

FIGS. 12-14 illustrate another form of releasable connection 50, which may be applied to along external surface of the balloon 12, such as working surface W, in order to maintain one or more folds 32. As can be appreciated from FIGS. 13 and 14, the connection 50 may be established by connecting a retainer 52 to the balloon 12, such as to the surface of the balloon wall 28 (inner or outer). The retainer 52 includes offset openings 54, as perhaps best understood in FIG. 14. Each opening 54 is adapted to receive an interleaving portion 56 when the retainer is attached to the balloon 12 along end portions 58, 60, as well as an intermediate portion 62, and the balloon wall 28 is folded. As can be appreciated, the interleaving portions 56 when interdigitated thus form a loop 62 through which an object, such as line 34, may be inserted. The line 34 thus holds the retainer 52 in a position to maintain the folds 32 in place, until withdrawn (such as from a remote location external to the body and through a lumen in the catheter).

Upon withdrawal of the line 34 from the loop 62, the retainer 52 may relax or expand to release the underlying folds 32 and thereby increase the diameter of the balloon 12. As can be appreciated, more than one such releasable connections 50 may be associated with the balloon 12, such as by being circumferentially spaced. The use of multiple connections 50 may provide for a single larger diameter on expansion, or multiple larger diameters, which may be selectively controlled by the clinician to provide the desired adjustability for different diameters of vessels.

FIG. 15 illustrates that the balloon 12 may be provided with a releasable connection 60 in the form of a jacket 62 over the balloon 12, and along the barrel section 16, in particular. The jacket 62 may be provided with releasably connected sections 62a, 62b, which may be connected by a frangible connection, such as for instance perforations 64. Pressurization of the balloon 12 to an inflation pressure insufficient to break the connection (perforation 64) would thus maintain the balloon at a first diameter, and further pressurization to a second inflation pressure (such as beyond a range associated with maintaining the first diameter) would break the connection and thus allow the balloon to expand in situ.

A further embodiment is described with reference to FIG. 16. In this embodiment, the balloon 12 is provided with one or more outwardly directed folds 32 (three shown). The releasable or frangible connection 70 is established within the folds along the interior of the balloon 12, which may be done during the process of forming the balloon from a sheet of material. The connection 70, which may be an adhesive or the other forms described herein, is such that pressurization of the balloon 12 to an inflation pressure that is not sufficient to break the connection would thus maintain the balloon at a first diameter, and further pressurization to a second pressure level (beyond a range) would break the connection and thus allow the balloon to expand in situ during a procedure.

The foregoing discussion is intended to provide an illustration of the inventive concepts, and is not intended to limit the invention to any particular mode or form. Any elements described herein as singular can be pluralized (i.e., anything described as "one" can be more than one), and plural elements can be used individually. Characteristics disclosed of a single variation of an element, the device, the methods, or combinations thereof can be used or apply for other variations, for example, dimensions, burst pressures, shapes, materials, or combinations thereof. Any species element of a genus element can have the characteristics or elements of any other species element of that genus. "Substantially" means that the value may vary depending on the circumstances. The above-described configurations, elements or complete assemblies and methods and their elements for carrying out the invention, and variations of aspects of the invention can be combined and modified with each other in any combination (for instance, the various connections described can be combined in any manner for use in connection with a single balloon), along with any obvious modifications.

The invention claimed is:

1. An apparatus for performing a medical procedure, comprising:
    a balloon comprising an inflatable body having a first fold held in place by a plurality of releasable connections including a first releasable connection and a second releasable connection, wherein the first releasable connection is adapted to disconnect at a first inflation pressure to allow the balloon to expand from a first diameter when the first fold is held in place by the first and second releasable connections to a second diameter greater than the first diameter, and the second releasable connection is adapted to disconnect at a second inflation pressure greater than the first inflation pressure to allow the balloon to expand from the second diameter to a third diameter greater than the second diameter.

2. The apparatus of claim 1, wherein the first releasable connection is adapted to hold the first fold in place while the balloon is inflated to a nominal diameter for treatment.

3. The apparatus of claim 1, wherein the first fold includes a recessed portion between adjacent lobes of the balloon, each of the lobes including a portion of the first releasable connection.

4. The apparatus of claim 1, wherein the first releasable connection comprises a frangible connection.

5. The apparatus of claim 1, wherein the releasable connection is adapted to be manually released by an actuator adapted for being remotely controlled by a clinician.

6. The apparatus of claim 1, wherein the first releasable connection comprises an adhesive.

* * * * *